(12) United States Patent
Jain et al.

(10) Patent No.: US 7,371,412 B2
(45) Date of Patent: May 13, 2008

(54) **PHARMACEUTICAL COMPOSITIONS COMPRISING AN EXTRACT OF *EUPHORBIA PROSTRATA***

(75) Inventors: Rajesh Jain, New Delhi (IN); Kour Chand Jindal, New Delhi (IN); Sukhjeet Singh, New Delhi (IN); Aniruddha Datta, New Delhi (IN)

(73) Assignee: Panacea Biotec Limited, New Delhi (IN)

( * ) Notice: Subject to any disclaimer, the term of this patent is extended or adjusted under 35 U.S.C. 154(b) by 0 days.

(21) Appl. No.: 10/551,797

(22) PCT Filed: Dec. 31, 2004

(86) PCT No.: PCT/IN2004/000445

§ 371 (c)(1),
(2), (4) Date: Sep. 29, 2005

(87) PCT Pub. No.: WO2005/065696

PCT Pub. Date: Jul. 21, 2005

(65) Prior Publication Data

US 2006/0198905 A1    Sep. 7, 2006

(30) Foreign Application Priority Data

Jan. 1, 2004   (IN) .............................. 5/DEL/2004

(51) Int. Cl.
*A61K 36/00* (2006.01)

(52) U.S. Cl. ..................................................... 424/725

(58) Field of Classification Search .................... None
See application file for complete search history.

(56) References Cited

U.S. PATENT DOCUMENTS 5,858,371 A * 1/1999 Singh et al. ................ 424/731

FOREIGN PATENT DOCUMENTS

EP        0868914 A1 * 1/1997

* cited by examiner

*Primary Examiner*—Christopher R. Tate
*Assistant Examiner*—Melenie McCormick
(74) *Attorney, Agent, or Firm*—Ladas and Parry LLP

(57) ABSTRACT

The invention relates to novel compositions comprising of an extract of the plant *Euphorbia prostrata*, particularly with pharmaceutically acceptable carrier(s)/base(s), optionally with additional therapeutic agent(s) useful for the treatment of anorectal disease and colonic diseases such as hemorrhoids, fissures, cracks, fistulas, abscesses, inflammatory bowel disease, and the like. The novel compositions possess properties to control inflammation, prevent capillary bleeding and fragility in mammalians, particularly human beings. Process for the preparation of such novel compositions comprising an extract of the plant *Euphorbia prostrata* and pharmaceutically acceptable carrier(s)/base(s) useful for the treatment of anorectal disease including hemorrhoids, and colonic diseases are also provided. The composition comprise of flavonoidal and phenolic constituents extracted from the plant *Euphorbia prostrata* that possess anti-inflammatory, analgesic, haemostatic and wound-healing properties.

12 Claims, 9 Drawing Sheets

Figure 1:
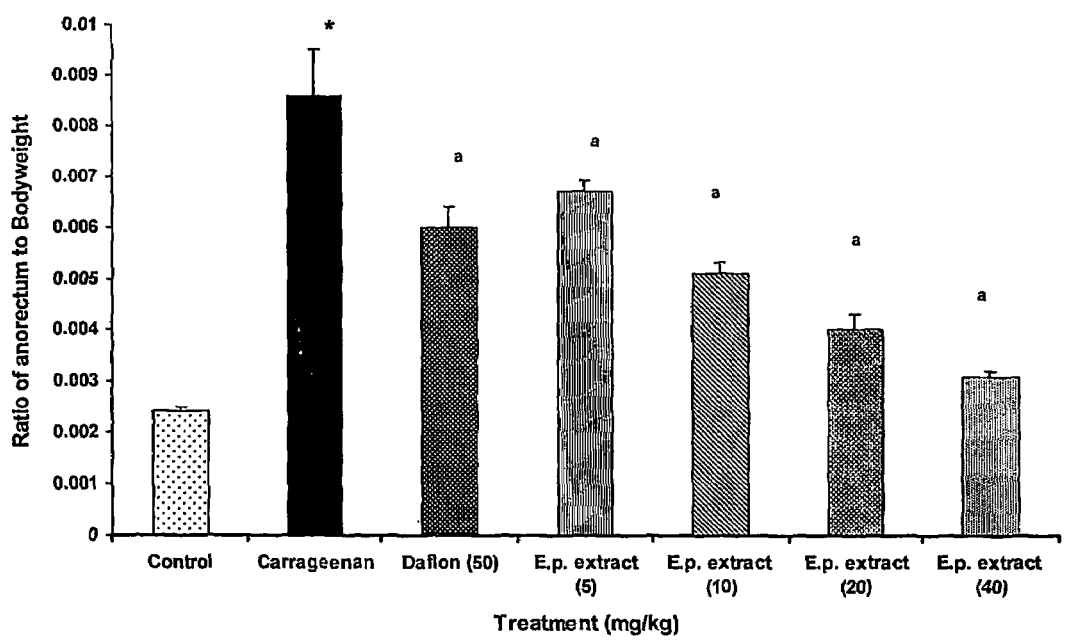

*p < 0.05 as compared with control group, a p < 0.05 as compared with carrageenan-treated group,*

*p < 0.05 as compared with control group, a p < 0.05 as compared with carrageenan-treated group

*p < 0.05 as compared with control group*

*$p < 0.05$ as compared with control group

*p < 0.05 as compared to the control group*

* $p < 0.05$ as compared to the control group a $p < 0.05$ as compared to the control group
* $p < 0.05$ as compared to the carrageenan treated group

PHARMACEUTICAL COMPOSITIONS COMPRISING AN EXTRACT OF *EUPHORBIA PROSTRATA*

FIELD OF THE INVENTION

The invention relates to novel compositions and process for preparation of such compositions comprising an extract of the plant *Euphorbia prostrata* useful for the treatment of anorectal diseases including hemorrhoids, and colonic diseases. The novel compositions possess properties to control inflammation, prevent capillary bleeding and fragility in mammalians, particularly human beings. Use of such compositions for the treatment of anorectal diseases including hemorrhoids, and colonic diseases are also provided.

BACKGROUND OF THE INVENTION

Among the various anorectal and colonic diseases, hemorrhoids occupy a prominent position and have been the subject of numerous clinical studies. Hemorrhoidal disease is characterised by bleeding, without any pain. Fresh blood spots occur immediately, on defecation. However, pain occurs when the hemorrhoids are secondarily infected, or complicated by thrombosis and anal fissures. Hemorrhoids can be caused by a variety of factors including hormones, genes, inflammation, infection, constipation, exercise, vascular stasis, diet, strain, physical stance in defecation, loss of connective tissue elasticity with age etc. The symptoms most widely recognized are bleeding, pain and prolapse (Hyams and Philpot, 1970; Smith, 1987). These may be accompanied by thrombosis, pruritis, edema etc. Hemorrhoids can be treated through reduction of inflammation and pain, haemostasis, wound healing and protection of vascular walls. Thus, an effective treatment of acute hemorrhoidal attacks should not only provide relief as early as 2-3 days after initiation of the treatment, but also reduce the recurrence of such attacks.

There exist several procedures for the treatment of hemorrhoids. WO8803398 patent application discloses surgical dressings for such treatment. Patents have been granted in respect of surgical devices such as European patent no. 0095142. U.S. Pat. No. 4,621,635 has been granted for the use of lasers in the treatment of hemorrhoids. The techniques of cryopharmacotherapy and electrochemical techniques for treatment of hemorrhoids have also been patented vide European patent no. 0091405 and European patent no. 0116688, respectively. However, the biggest drawbacks of the above are the involvement of medical experts beyond mere prescription of medicines and probable hospitalization. Also, some of them are physically and/or psychologically unpleasant in application for treating such diseases.

Several patents (U.S. Pat. Nos. 4,160,148, 4,508,728, 4,797,392, 4,518,583 and 5,234,914) have been granted in respect of compositions containing certain wound healing agents to provide symptomatic relief, by promoting tissue repair, reducing inflammation and encouraging wound healing. Some of them like U.S. Pat. Nos. 4,518,583 and 5,234,914 contain antimicrobial agents. These compositions, however, only relieve symptoms associated with inflammation, like heat, itching, redness, pain and swelling.

A number of compositions for the treatment of anorectal diseases (including hemorrhoids) are based on the anesthetic and vasoconstrictive properties of the constituents, but these provide only temporary symptomatic relief.

Patents in the United States of America (U.S. Pat. Nos. 4,613,498, 4,626,433, 5,166,132, 5,219,880, 5,234,914 and 4,797,392) and Europe (European patents nos. 0225832 and 0513442) have been granted in respect of compositions with varying constituents, for topical application in the form of suitable and acceptable pharmaceutical carriers, such as salts, ointments, etc., with organic, inorganic or biological active agents. However, these compositions provide only temporary relief and are limited to local application and cannot be used for systemic use or oral administration.

A topical treatment for hemorrhoidal pain and for spasms of the sphincters and muscles located in the GI tract is disclosed in a granted patent (U.S. Pat. No. 5,595,753), which includes amino acid L-arginine in a pharmaceutically acceptable carrier. Another U.S. Pat. No. 5,591,436 has been granted for a composition for dietary supplement for the treatment of hemorrhoids. The composition comprises 60% to 95% Indian Barberry by weight; 4.8% to 38% Nagkesar by weight; and 0.2% to 2% Margosa tree leaves by weight.

Another U.S. Pat. No. 5,562,906 discloses the use of bark or berries of the species *Xanthoxylum clava herculis* L and *Xanthoxylum americanum* Hill, both of the yellow wood tree family, are employed for the treatment of hemorrhoids and other membrane and capillary disorders of the veins and arteries. Improved strength and flexibility of the veins, arteries and their constituent structures is obtained.

The flavonoidal constituents present in the extract of *Euphorbia Prostrata* are reported to have anti-inflammatory properties. The phenolic compounds like ellagic and gallic acids and tannins are reported to have anti-inflammatory, haemostatic, gastro-protective and wound healing properties.

Other plants containing flavonoids including apigenin glycosides and luteolin glycosides are *Ixora arborea* (Rubiaceae), *Bommeria hispida* (Pteridaceae), *Adenocalymma alliaceum* (Bignoniaceae), *Thalictrum thunbergii* (Ranunculaceae), *Perilla frutescens* (Labiateae), *Chrysenthemum indicum, C. coronarium* and *Matricaria chamomilla* (Compositae), *Thymus membranaceous* (Labiateae), *Digitalis lanata* (Scrophulariaceae), *Cuminum cyminum* and *Petroselinum* (Umbelliferae). Several species of *Euphorbia* like *Euphorbia minuta, Euphorbia microphylla, Euphorbia granulata* (Euphorbiaceae) contain both apigenin and luteolin. Ellagic acid and other phenolic acids have been reported from different species of *Euphorbia*.

The safety of various components of the *Euphorbia* extract has been reported in the literature. Some of the reports also claim anti-mutagenic/anti-carcinogenic/anti-genotoxic properties of the components of the *Euphorbia* extract.

An Indian Pat. No. 186803 and several other patents (Australia, No. 698407; China, No. CN 1102387C; Europe, No. 868914; Russia, No. 2174396; South Africa, No. 97/2900; South Korea, No. 281679 and U.S., Pat. No. 5,858,371) have been granted to this applicant for a composition comprising a flavonoid containing extract of *Euphorbia prostrata* for treatment of anorectal and colonic diseases. However, the presence of the phenolic compounds those are therapeutically useful for treatment of anorectal and colonic diseases due to their hemostatic and astringent properties, did not exist in the claimed extract. The process of extraction claimed in the said patent comprised of an intermediate step of treating the concentrated extract with hot water (80-90° C.); which resulted in the loss of especially the phenolic compounds from the extract, since they were washed out with the water. It has been surprisingly found by the inventors of the present invention that the presence of the phenolic compounds like ellagic acid, gallic acid and tannins comprising of these acids makes the claimed extract more effective for treatment of hemorrhoids and other colonic diseases, as the phenolic compounds are known mucoprotective agents. The antimicrobial properties of these phenolic compounds further prevent secondary infections often accompanied with hemorrhoids, fissures, fistulas etc. The present invention describes an improved process for the preparation of the *Euphorbia prostrata* extract thus resulting in an improved composition of the said extract. The previously essential step of treatment of the concentrated extract with hot water has been removed in the present invention since it was found that the water soluble portion contains substantial amount of phenolic compounds; instead washing the said concentrated extract was done directly with non-polar solvent where only waxy materials and pigments are removed and there is no significant loss of phenolic compounds, followed by preferably re-extracting the washed polar extract in a medium polarity organic solvent followed by distilling, dehydrating and finally drying the extract.

The inventors have further researched, and have found that the novel flavonoid and phenolic compounds containing extract of *Euphorbia prostrata* disclosed in the present invention exhibits improved pharmacological response in comparison to existing compositions employing flavonoids either from *Euphorbia* or other sources. Further, the extraction procedure of the disclosed *Euphorbia Prostrata* extract in the present invention is more cost effective and less time consuming in comparison to that of existing compositions employing flavonoids isolated from *Euphorbia prostrata*. The commercial implications of the improved and economic extraction procedure led the inventors to re-establish the pharmacological and toxicological validity of the new extract. The results were strikingly better than those of the equivalent flavonoid doses of the more purified extract of *Euphorbia prostrata* as disclosed earlier.

The present invention provides pharmaceutical compositions for the long-term management of anorectal diseases including hemorrhoids, and colonic diseases that are safe and painless to administer and have long-term effectiveness. The compositions of the present invention have improved efficacy and safety and are economical to manufacture.

SUMMARY OF THE INVENTION

An objective of the present invention is to provide pharmaceutical composition for the treatment of anorectal or colonic disease such as hemorrhoids, fissures, cracks, fistulas, abscesses, inflammatory bowel disease, and the like comprising of an extract of the plant *Euphorbia prostrata* containing flavonoids and phenolic compounds, wherein the flavonoids are apigenin-7-glycoside, 1-4% by weight; luteolin-7-glycoside, 0.3-2% by weight; and apigenin, luteolin and quercetin, 0.001-0.3% by weight; and wherein the phenolic compounds are ellagic acid, 1-15% by weight; gallic acid, 1-12% by weight and tannins, 1-10% by weight, optionally with pharmaceutically acceptable carrier(s)/base(s); optionally with additional therapeutic agent(s); and wherein the pharmaceutical composition comprise of the extract of the plant *Euphorbia Prostrata* from about 0.1% to about 99% by weight.

It is also an objective of the present invention to provide process for the preparation of an extract of the plant *Euphorbia prostrata* for the treatment of anorectal or colonic disease such as hemorrhoids, fissures, cracks, fistulas, abscesses and inflammatory bowel disease.

It is a further objective of the present invention to provide process for the preparation of pharmaceutical composition for the treatment of anorectal or colonic disease such as hemorrhoids, fissures, cracks, fistulas, abscesses and inflammatory bowel disease comprising of an extract of the plant *Euphorbia prostrata* containing flavonoids and phenolic compounds, wherein the flavonoids are apigenin-7-glycoside, 1-4% by weight; luteolin-7-glycoside, 0.3-2% by weight; and apigenin, luteolin and quercetin, 0.001-0.3% by weight; and wherein the phenolic compounds are ellagic acid, 1-15% by weight; gallic acid, 1-12% by weight and tannins, 1-10% by weight, with pharmaceutically acceptable carrier(s)/base(s) as herein described, optionally with additional therapeutic agent(s) as herein described, comprising of the following steps.

a. drying the plant *Euphorbia Prostrata* under controlled conditions of temperature and humidity,
b. making a powder from the dried plant,
c. extracting the dry coarse powder with a polar solvent repetitively to form an extract,
d. distilling the extract,
e. washing the concentrated extract with a non-polar organic solvent, and
f. drying the washed extract to produce the desired pharmaceutically acceptable extract capable of being used along with pharmaceutically acceptable carrier(s)/base(s).

Yet another objective of the present invention is to provide method of using such pharmaceutical compositions for the treatment of anorectal or colonic disease such as hemorrhoids, fissures, cracks, fistulas, abscesses, and inflammatory bowel disease.

The compositions of the present invention and method for treating anorectal diseases including hemorrhoids and colonic diseases using an extract of the plant *Euphorbia prostrata* provides long-term effectiveness and low prolapse rates.

DETAILED DESCRIPTION OF THE INVENTION

The present invention provides compositions that can be orally administered as well as uniformly applied to the affected region. It reduces inflammation, and soothes the feeling of itching and burning associated with it. The invention provides relief from pain associated with hemorrhoids. The invention also significantly reduces bleeding and accelerates tissue re-growth in the affected hemorrhoidal tissue. The invention is useful in the treatment of lesions, other than hemorrhoids in the anorectal area and can be formulated in several types of dosage forms. There are no side effects from the use of the composition in human beings. Further, the treatment is not physically or psychologically unpleasant in its administration and/or application. The plant *Euphorbia prostrata* (Family: Euphorbiaceae) was identified as being relevant in the study of anorectal and colonic diseases, including hemorrhoids. *Euphorbia prostrata* is well known to the Indian traditional medicine in the use of treatment for asthma, bloody dysentery, and sores. Previously, five new compounds were discovered and identified by the inventors in *Euphorbia prostrata* namely luteolin, 6-methoxy-quercetin-glycoside, quercetin, and glycosides of luteolin and apigenin. Now two more phenolic compounds, namely ellagic acid and gallic acid were identified in the extract prepared in a different manner, which were found to be of additional therapeutic value for treatment of hemorrhoids.

The compounds of the present invention are standardized to pharmaceutically acceptable specifications in order to ensure reproducibility from batch to batch. The result is the improved extract of *Euphorbia prostrata*, which is particularly the active ingredient of the present pharmaceutical compositions for the effective management of anorectal and colonic diseases. Another unique feature of this extract of *Euphorbia prostrata* is that it is prepared in such a manner that the resulting composition is easily dispersible in water due to presence of many hydrophilic compounds besides flavonoids.

The pharmaceutical composition comprising of the extract of *Euphorbia prostrata* as the active ingredient comprises flavonoids and phenolic compounds, out of which apigenin-7-glycoside is about 1-4% by weight of the extract, luteolin-7-glycoside is about 0.3-2% by weight of the extract, and apigenin, luteolin and quercetin are about 0.001-0.3% by weight of the extract. The extract also comprises 1-15% by weight of ellagic acid, 1-12% by weight of gallic acid, and tannins, 1-10% by weight.

In a preferred embodiment of the present invention, is provided a pharmaceutical composition, wherein the extract comprises preferably 2.5-3.5% by weight apigenin-7-glycoside, 0.5-1.5% by weight luteolin-7-glycoside, 0.05-0.2% by weight apigenin, luteolin and quercetin, 4-15% by weight ellagic acid, 4-12% by weight gallic acid and 3-8% by weight tannins.

In a further embodiment, the pharmaceutical composition of the present invention further comprises pharmaceutically acceptable carrier(s)/base(s) selected from but limited to the group comprising of diluents, disintegrants, binders, antiadherants, glidants, anti-oxidants, buffering agents, colorants, flavoring agents, coating agents, solvents, viscosifying agents, waxes, wetting agents, emulsifying agents, solubilizers, stabilizers, buffering agents, and the like.

In an embodiment of the present invention, *Euphorbia prostrata* was found to be devoid of any toxic diterpene content like phorbol or ingenol esters, unlike many other species of *Euphorbia*.

The pharmaceutical compositions of the present invention may also contain additional therapeutic agents from other plants and/or from different pharmacological groups such as anesthetics, vasoconstrictors, protectants, counterirritants, astringents, wound healing agents, antimicrobials, keratolytics, anticholinergics or their pharmaceutically acceptable salts, used either alone or in combinations thereof. Preferably, it would be beneficial to include other wound healing and antimicrobial agents, which will result in the improvement of the effectiveness of the composition.

The anesthetics include but are not limited to benzocaine, diperodon, pramoxine, camphor, dibucaine, phenol, tetracaine, lignocaine and phenacaine, used either alone or in combinations thereof. The amount of such anesthetics could vary between 0.25% and 25% by weight.

The vasoconstrictors include but are not limited to ephedrine and phenylephrine, used either alone or in combinations thereof. The amount of such vasoconstrictors may vary between 0.005% and 1.5% by weight.

The protectants include but are not limited to aluminum hydroxide gel, calamine, cocoa butter, cod or shark liver oil, glycerin in aqueous solution, kaolin, lanolin, mineral oil, starch, white petroleum, wool alcohol, zinc oxide, vegetable or castor oil, polyethylene glycol and propylene glycol, used either alone or in combinations thereof. The amount of such protectants may vary between 5.0% and 88.0% by weight.

The counterirritant includes but is not limited to menthol in aqueous solution. The amount of such counterirritant may vary between 0.25-2.5% by weight.

The astringents include but are not limited to calamine, zinc oxide, *hamamelis* water, bismuthresorcinol compound, bismuth subgallate, Peruvian balsam, aluminium chlorhydroxy allantoinate, tannic acid and tannins, used either alone or in combinations thereof. The amount of such astringents may vary between 0.2% and 60.0% by weight. The tannins additionally may be derived from plants such as *Butea monosperma, Butea parviflora* and *Butea frondoza* (Family: Leguminosae).

The wound healing agents include but are not limited to vitamin A and vitamin D in an amount of between 0.005% and 0.04% by weight. Also Peruvian balsam can be included by weight in an amount of between 0.5% and 2.5% by weight. Also cod liver oil can be included in an amount between 1.0% and 6.0% by weight.

The antimicrobial agents include but are not limited to benzethonium chloride, benzalkonium chloride, boric acid, 8-quinolinol benzoate, secondary amyltricresols, cetylpyridinium chloride, phenol, menthol, chlorothymol, camphor and 8-hydroxyquinoline sulfate, used either alone or in combinations thereof. The amount of such antimicrobial agents may vary between 0.02% and 40.0% by weight.

The keratolytics include but are not limited to aluminium chlorhydroxy allantoinate and resorcinol, used either alone or in combinations thereof. The amount of such keratolytics may vary between 0.2% and 3.5% by weight.

The anticholinergics include but are not limited to atropine or other solanaceous type alkaloids, used either alone or in combination thereof. The amount of such anticholinergics may vary between 0.02% and 0.1% by weight.

The pharmaceutical compositions of the present invention can be prepared by dissolving or dispersing the extract in appropriate base(s)/carrier(s) known to the art. The pharmaceutical composition into different dosage forms can be formulated using conventional excipients and techniques known to art. Pharmaceutical dosage forms of the present invention can be capsules (hard or soft), tablets (coated or uncoated), ointments, creams, gels, foams, solutions, suspensions, medicated pad, bandage, powder, aerosols, sprays, film, flakes, modified release dosage forms (sustained release, controlled release, delayed release, prolonged release, timed release, and the like) sublingual dosage forms, wafers, caplets, parenteral dosage forms to be infiltrated at the site of the injection, and the like. The pharmaceutical compositions of the present invention comprise of the extract of the plant *Euphorbia prostrata* from about 0.1% to about 99% by weight.

The capsules comprise of 25-300 mg of the extract of *Euphorbia prostrata*, preferably 50-100 mg along with pharmaceutical excipients. Similarly, tablets may be prepared by dispersing 25-300 mg of the extract of *Euphorbia prostrata*, preferably 50-100 mg in a suitable carrier, optionally along with other pharmaceutical excipients. The tablets may be coated or uncoated. The cream or ointment comprises 0.1-10% w/w, preferably 0.2-5% w/w of the extract of *Euphorbia prostrata*.

In an embodiment of the present invention, the capsule may be taken, subject to a maximum of 300 mg of extract per day, along with topical application comprising the same extract, as and when required. In another embodiment, the granules in ready dispersible and effervescent form are prepared by using excipients such as sucrose, mannitol, sodium bicarbonate, citric acid, and the like.

The cream comprising the extract of *Euphorbia prostrata* is prepared by emulsifying the aqueous phase, comprising 0.1-10% w/w preferably 0.2-5% w/w of the extract, along with a suitable oleaginous phase.

Other alternatives can be prepared by formulating the extract in 0.1-10% w/w as Hydrophilic ointment USP with absorption bases; or water soluble bases such as Polyethylene glycol ointment USNF; or as water absorbing bases such as Hydrophilic petrolatum USP, Lanolin USP; or in hydrocarbon bases such as White petrolatum USP.

The suppository compositions comprises either hydrophobic or hydrophilic base and includes cocoa butter, glycerinated gelatin, hydrogenated vegetable oils, mixtures of polyethylene glycols of various molecular weights, polyoxyethylene sorbitan fatty acid esters and polyethylene stearates, polyvinyl alcohol, polyvinyl pyrrolidone, polyacrylamide, chemically modified starch or a combination of these materials.

The foam and spray bases comprises one or more of aqueous and nonaqueous solvents, propellants, surfactants, suspending agents and stabilizing agents.

The medicated pads comprise one or more of the following: Water, glycerin, propylene glycol, alcohol and *Hamamelis* water.

In an embodiment of the present invention, is provided a process for the preparation of a pharmaceutical composition for the treatment of anorectal or colonic disease such as hemorrhoids, fissures, cracks, fistulas, abscesses and inflammatory bowel disease comprising of an extract of the plant *Euphorbia prostrata* containing flavonoids and phenolic compounds, wherein the flavonoids are apigenin-7-glycoside, 1-4% by weight; luteolin-7-glycoside, 0.3-2% by weight; and apigenin, luteolin and quercetin, 0.001-0.3% by weight; and wherein the phenolic compounds are ellagic acid, 1-15% by weight; gallic acid, 1-12% by weight and tannins, 1-10% by weight, with pharmaceutically acceptable carrier(s)/base(s) as herein described, optionally with additional therapeutic agent(s) as herein described, comprising of the following steps.
   a. drying the plant *Euphorbia prostrata* under controlled conditions of temperature and humidity,
   b. making a powder from the dried plant,
   c. extracting the dry coarse powder with a polar solvent repetitively to form an extract,
   d. distilling the extract,
   e. washing the concentrated extract with a non-polar organic solvent, and
   f. drying the washed extract to produce the desired pharmaceutically acceptable extract capable of being used along with pharmaceutically acceptable carrier(s)/base(s).

The polar solvent used in the present invention is selected from but not limited to acetone, methanol, ethanol, isopropanol, water, and the like used either alone or in combination thereof.

The non-polar organic solvent used in the present invention is selected from but not limited to pentane, hexane, heptane, petroleum ether, chloroform, dichloromethane, dichloroethane, or mixtures thereof.

In a further embodiment, is provided a process for the preparation of a pharmaceutical composition wherein the process for the manufacture of the extract further comprises:
   a. re-extracting the washed polar extract in a medium polarity organic solvent,
   b. distilling the extract,
   c. dehydrating the extract, and
   d. drying the extract to produce the desired pharmaceutically acceptable extract capable of being used along with pharmaceutically acceptable carrier(s)/base(s).

In the present invention, the medium polarity organic solvent is selected from but not limited to ethyl acetate, ethyl methyl ketone, butanol, or mixtures thereof.

The dehydration of the extract is preferably done by using a dehydrating agent selected from but not limited to anhydrous sodium sulphate, fused, calcium chloride, potassium aluminosilicate (molecular sieves), and the like used either alone or in combinations thereof. Dehydration may be done by physical processes like gravitational or centrifugal settling, with or without changing the temperature of the extract;

In an embodiment of the present invention, a method of treatment of anorectal or colonic disease such as hemorrhoids, fissures, cracks, fistulas, abscesses, inflammatory bowel disease, and the like, comprising administering an extract of the plant *Euphorbia prostrata* containing flavonoids and phenolic compounds, wherein the flavonoids are apigenin-7-glycoside, 1-4% by weight; luteolin-7-glycoside, 0.3-2% by weight; and apigenin, luteolin and quercetin, 0.001-0.3% by weight; and wherein the phenolic compounds are ellagic acid, 1-15% by weight; gallic acid, 1-12% by weight and tannins, 1-10% by weight, with pharmaceutically acceptable carrier(s)/base(s); optionally with additional therapeutic agent(s) is provided.

In a further embodiment, the pharmaceutically acceptable carrier(s)/base(s) used in the present invention is selected from but not limited to mannitol, lactose, microcrystalline cellulose, dibasic calcium phosphate, maltodextrin, cyclodextrin, and the like, used either alone or in combination thereof.

In another embodiment of the present invention, if the flavonoid and phenolic content of the extract obtained by the above method are more than the ranges specified herein, it is standardized by mixing with pharmaceutically acceptable carrier(s)/base(s) upto the desirable range of the contents.

In a further embodiment, use of an extract of the plant *Euphorbia prostrata* for the preparation of a pharmaceutical composition for the treatment of anorectal or colonic disease such as hemorrhoids, fissures, cracks, fistulas, abscesses, inflammatory bowel disease, and the like are provided.

The compositions of the present invention and method for treating anorectal diseases including hemorrhoids, and colonic diseases using an extract of *Euphorbia prostrata* provides long-term effectiveness and low prolapse rates. The treatment includes administration by oral route an effective amount of composition comprising of a pharmaceutically acceptable carrier and mixture of flavonoids and phenolic compounds extracted from *Euphorbia prostrata*. The treatment also includes local application to the hemorrhoids and anorectal tissues, an effective amount of composition comprising of a pharmaceutically acceptable carrier and a mixture of flavonoids and phenolic compounds extracted from *Euphorbia prostrata*.

Evaluation of Pharmacological Activity of the Extract

Antihaemorrhoidal Activity

Figure 2:
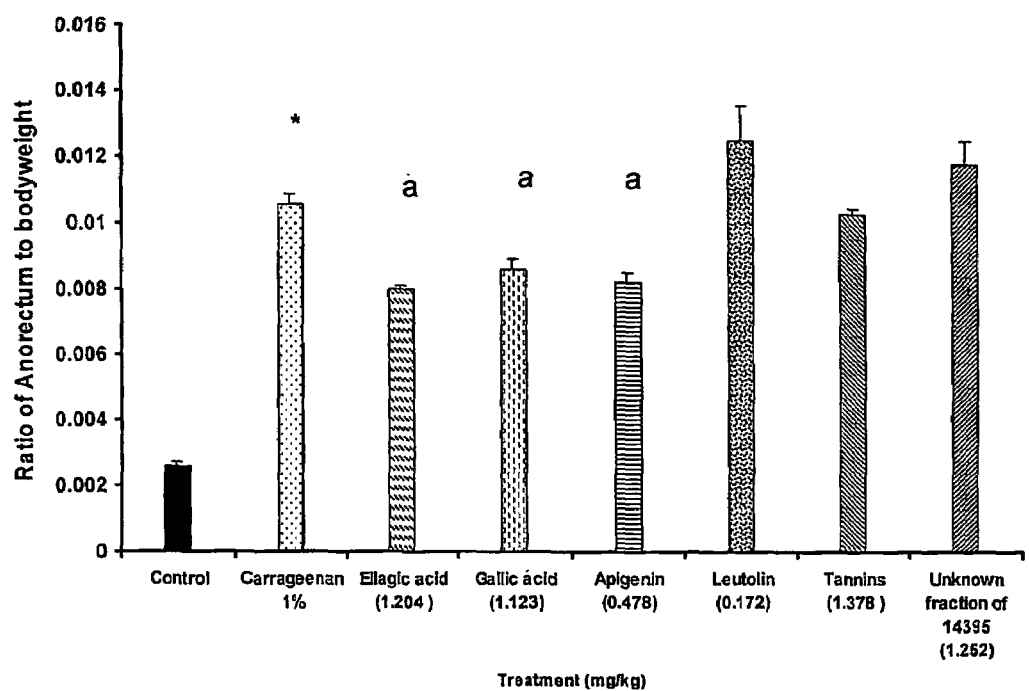

The antihaemorrhoidal activity of the *Euphorbia prostrata* extract was assessed and compared with reference drug, diosmin using anorectum:body weight ratio model in rats (modified method of Jia et al., 2000). *Euphorbia prostrata* extract (5, 10, 20 and 40 mg/kg, p.o., 7 days) showed significant decrease in anorectum:bodyweight ratio as well as inflammation and redness at the site when compared to control (carrageenan treated group). Diosmin (50 mg/kg, p.o., 7 days) also significantly decreased anorectal body weight ratio in rats (FIG. 1). Further, individual components of *Euphorbia prostrata* extract i.e. apigenin-7-glucoside (0.478 mg/kg, p.o.), ellagic acid (1.204 mg/kg, p.o.), and gallic acid (1.123 mg/kg, p.o.) on chronic administration (7 days) also showed effect (FIG. 2). In histopathological examination of the anorectum, normal animals administered per orally with 0.5% CMC alone showed intact mucosal layer with prominent mucosal cells and mild leukocyte migration, whereas carrageenan treated animals showed uneven thick mucosal layer with disrupted mucosal cells and severe leukocyte migration suggesting the presence of a significant inflammation. Further, both *Euphorbia prostrata* extract (10 mg/kg, p.o., 7 days) and diosmin (50 mg/kg, p.o., 7 days) showed intact mucosal layer with prominent mucosal cells and mild leukocyte migration.

Anti-inflammatory Activity

Carrageenan—Induced Paw Oedema in Rats

Figure 3:
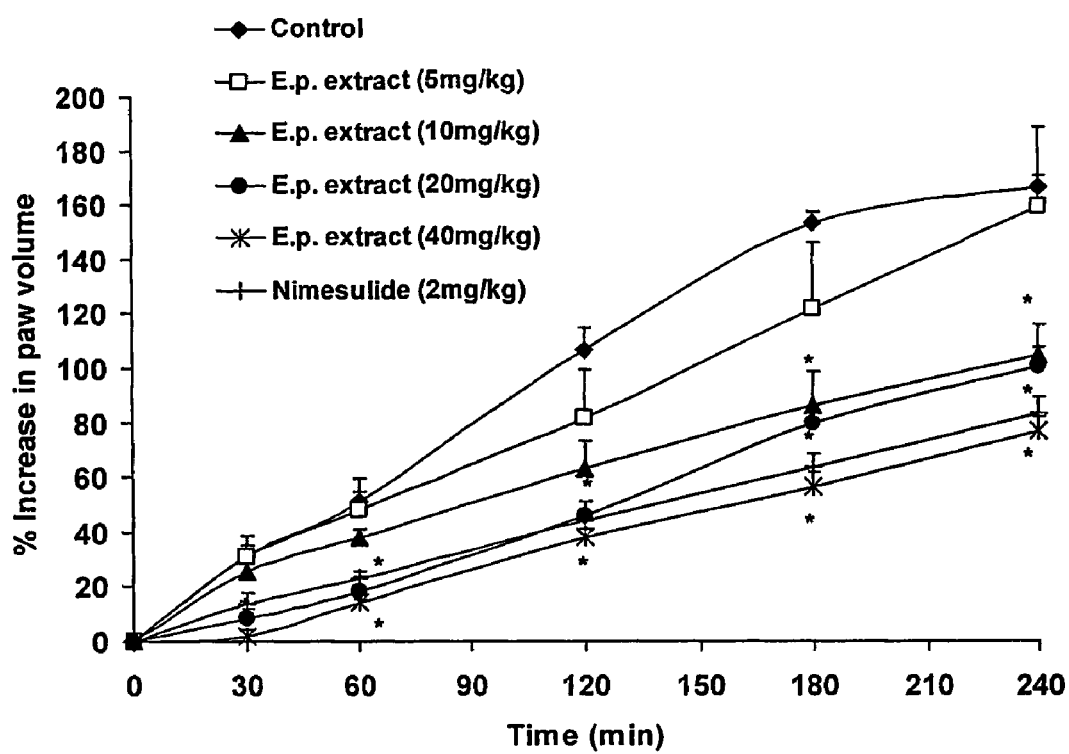
Figure 4:
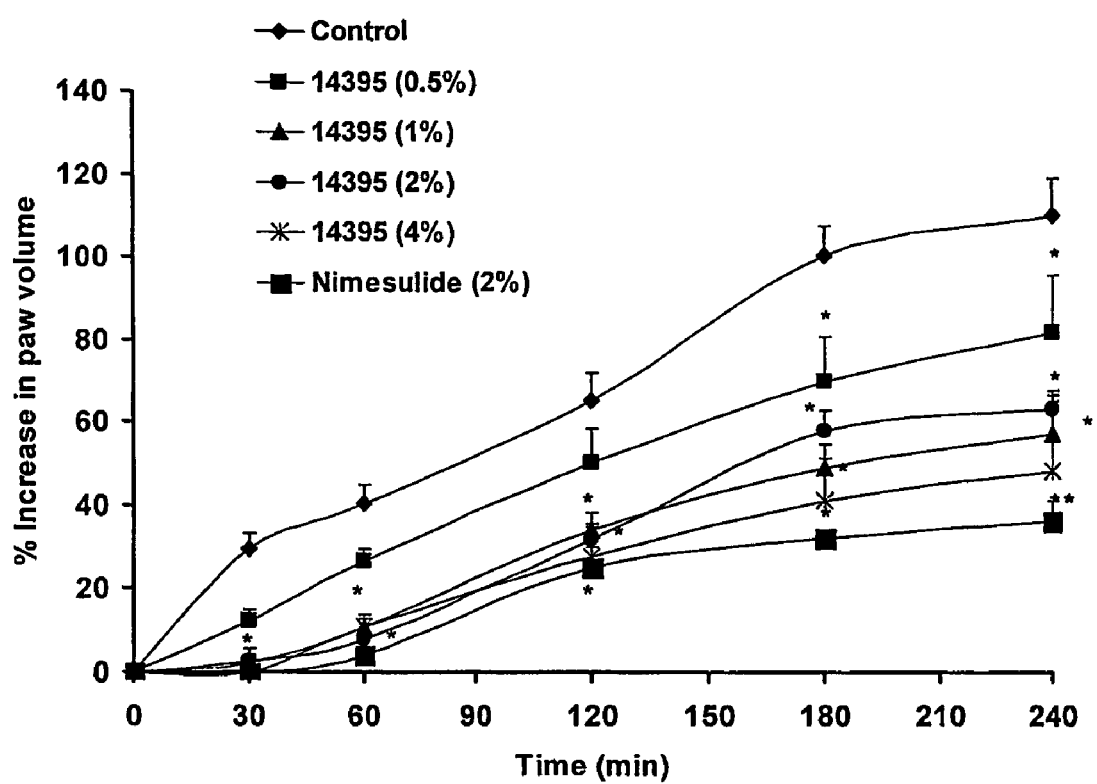

Carrageenan (1% w/v) produced paw oedema (Winter et al., 1962) in control group, indicating inflammatory response. *Euphorbia prostrata* extract (5, 10, 20, and 40 mg/kg, p.o.) dose dependently and significantly decreased carrageenan-induced increase in paw volume as compared to control rats ($ED_{50}$ 15.42-15.84 mg/kg, p.o.) The onset of anti-inflammatory effect was rapid and lasted up to 4 hrs after carrageenan injection. The anti-inflammatory effect of *Euphorbia prostrata* extract at doses 20 and 40 mg/kg was comparable to that of nimesulide (2 mg/kg, p.o.), a preferential cyclooxygenase-2 (COX-2) inhibiting NSAID (FIG. 3). Further, a solution of *Euphorbia prostrata* extract (0.5-4.0% w/v equivalent to 1-8 mg/kg, applied topically on paw) significantly decreased the carrageenan—induced increase in paw volume. The topical anti-inflammatory effect of *Euphorbia prostrata* extract (1%) was comparable to that of nimesulide (2%) at 60 min (FIG. 4).

Antinociceptive Activity

Acetic Acid—Induced Writhing in Mice (Koster et al., 1959)

Figure 5:
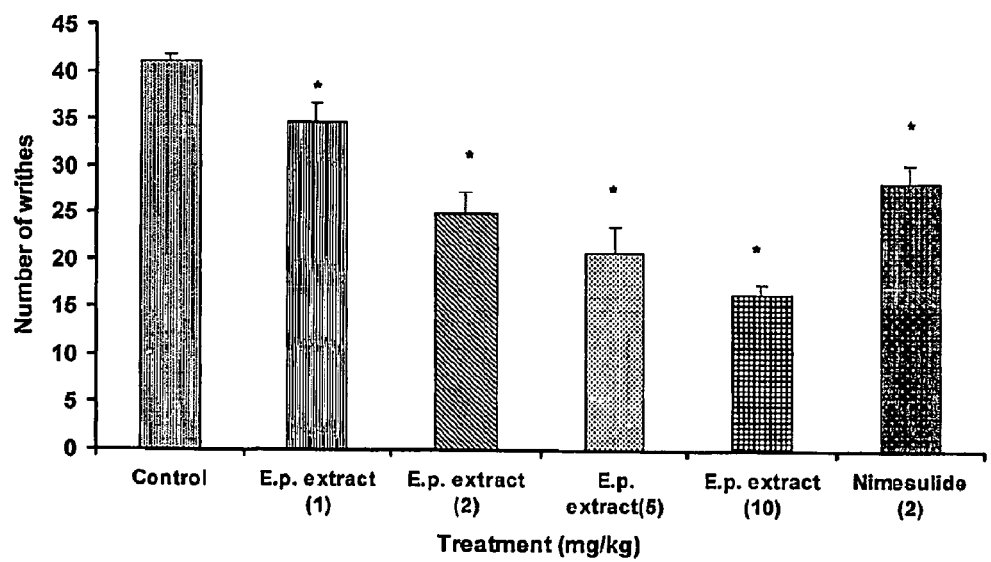
Figure 6:
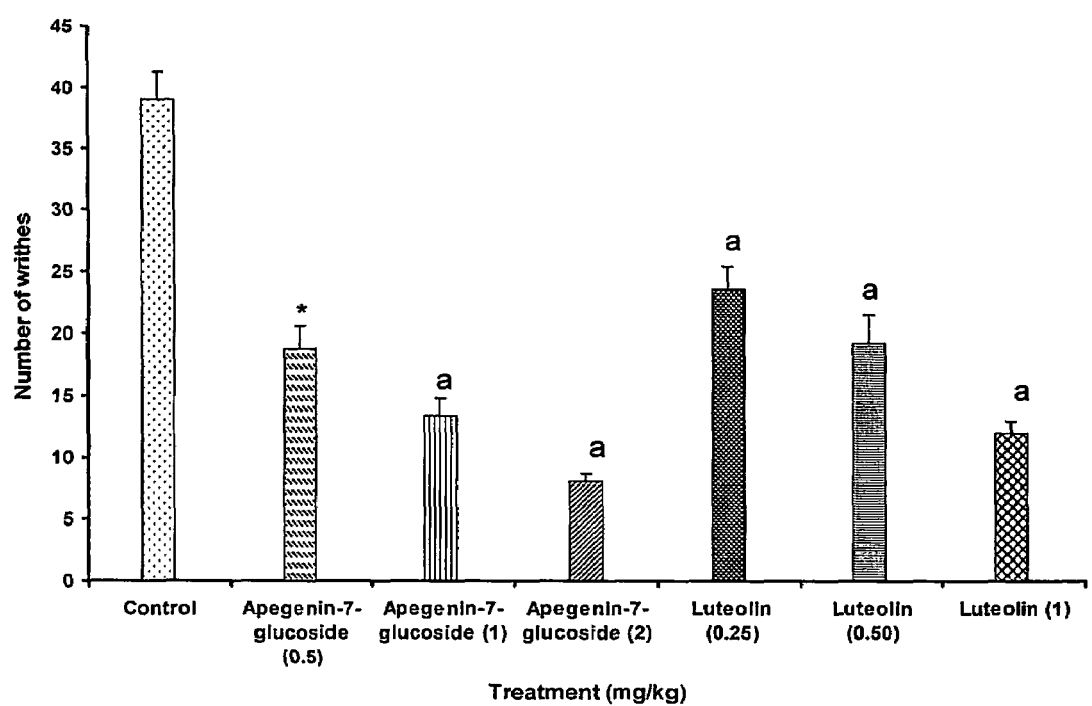

*Euphorbia prostrata* extract (2 mg/kg, p.o.) exhibited maximum antinociceptive effect after 90 minutes of its administration in time-response study. This effect lasted up to 2 hrs of its administration. Nimesulide (2 mg/kg), a reference drug also significantly increased the pain threshold in mice. *Euphorbia prostrata* extract (1, 2, 5, and 10 mg/kg, p.o.) produced dose—dependent antinociceptive effect in mice (FIG. 5). Apigenin-7-glucoside (0.5, 1.0, and 2.0 mg/kg, p.o.) and luteolin-7-glucoside (0.25, 0.5, and 1.0 mg/kg, p.o.) also exhibited dose-dependent antinociceptive effect in the writhing test (FIG. 6).

Carrageenan—Induced Hyperalgesia in Rats

Figure 7:
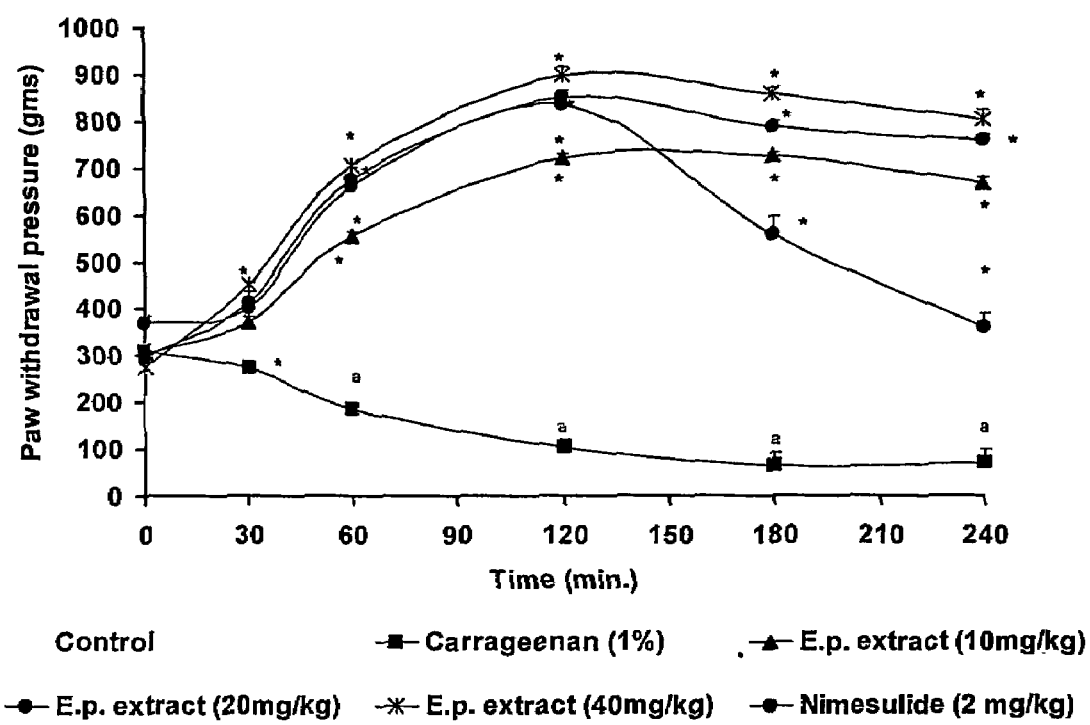

Carrageenan (1% w/v) significantly decreased paw withdrawal threshold in paw pressure test (Randall and Selitto, 1957). *Euphorbia prostrata* extract (10, 20, and 40 mg/kg, p.o.) significantly increased paw withdrawal threshold as compared to carrageenan treated rats, Nimesulide (2 mg/kg), a reference drug also increased paw withdrawal latencies in rats (FIG. 7).

Carrageenan—Induced Pleurisy in Rats

Pleurisy was induced with carrageenan (2%) using a method reported by Engelhard et al., 1995. A single dose administration of *Euphorbia prostrata* extract (10, 20 and 40 mg/kg, p.o.) produced significant inhibition of exudate formation and migration of polymorphonuclear leukocytes and monocytes in carrageenan-induced pleurisy. The results are shown in table-1.

TABLE 1

Effect of *Euphorbia prostrata* extract (E.p. extract) on cell migration in an animal model of pleurisy

| S. No. | Treatment (mg/kg, p.o.) | Exudate Volume (ml) | PMNs × $10^6$ | Monocytes × $10^6$ |
|---|---|---|---|---|
| 1. | Carrageenan (2%) | 3.10 ± 0.10 | 85.6 ± 2.10 | 18.4 ± 1.10 |
| 2. | E.p. extract (10) | 2.64 ± 0.03* | 76.4 ± 1.83 | 15.2 ± 1.68 |
| 3. | E.p. extract (20) | 2.56 ± 0.09* | 73.0 ± 2.31* | 13.0 ± 1.05* |
| 4. | E.p. extract (40) | 2.24 ± 0.05* | 54.8 ± 5.20* | 3.6 ± 0.90* |

*$p < 0.05$ as compared with carrageenan control group

Haemostatic Activity

Figure 8:
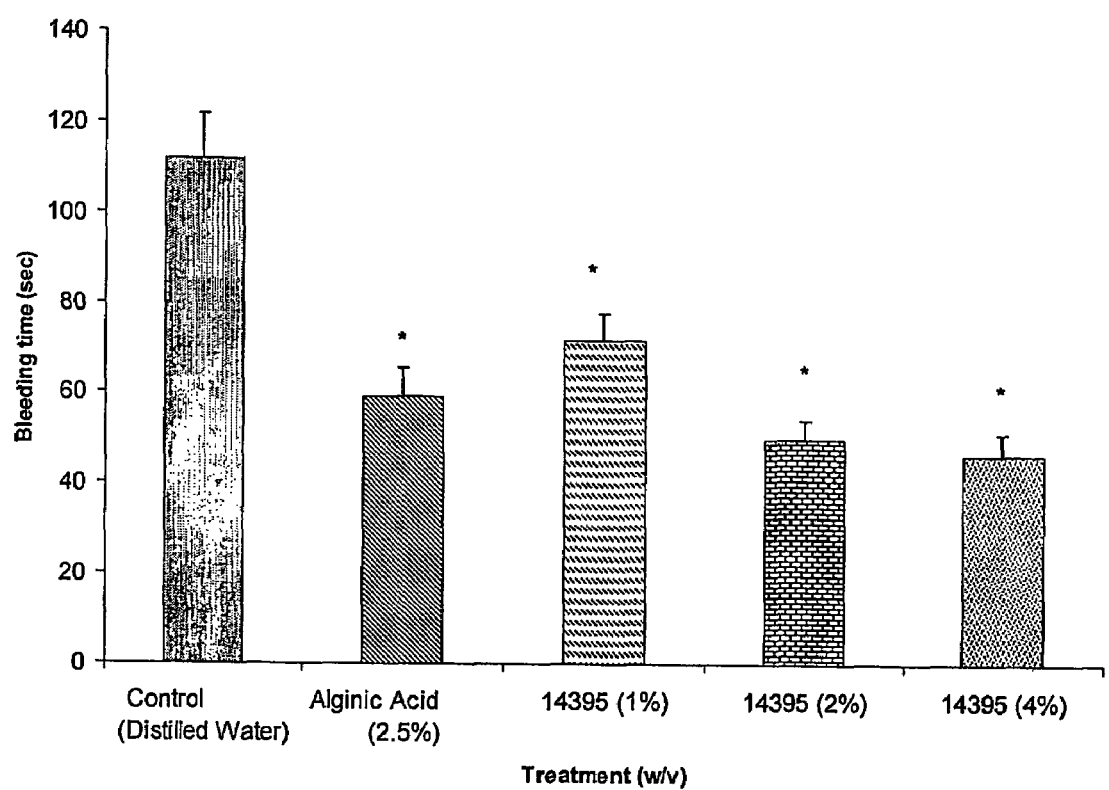

In a liver incision model, topical application of *Euphorbia prostrata* extract (1%, 2% and 4% solution) significantly reduced the bleeding time as compared to control group (distilled water). Further, the reduction in bleeding time observed with 4% solution of *Euphorbia prostrata* extract was comparable to that observed with alginic acid (2.5%) (FIG. 8).

Superoxide Radical Scavenging Activity

Figure 9:
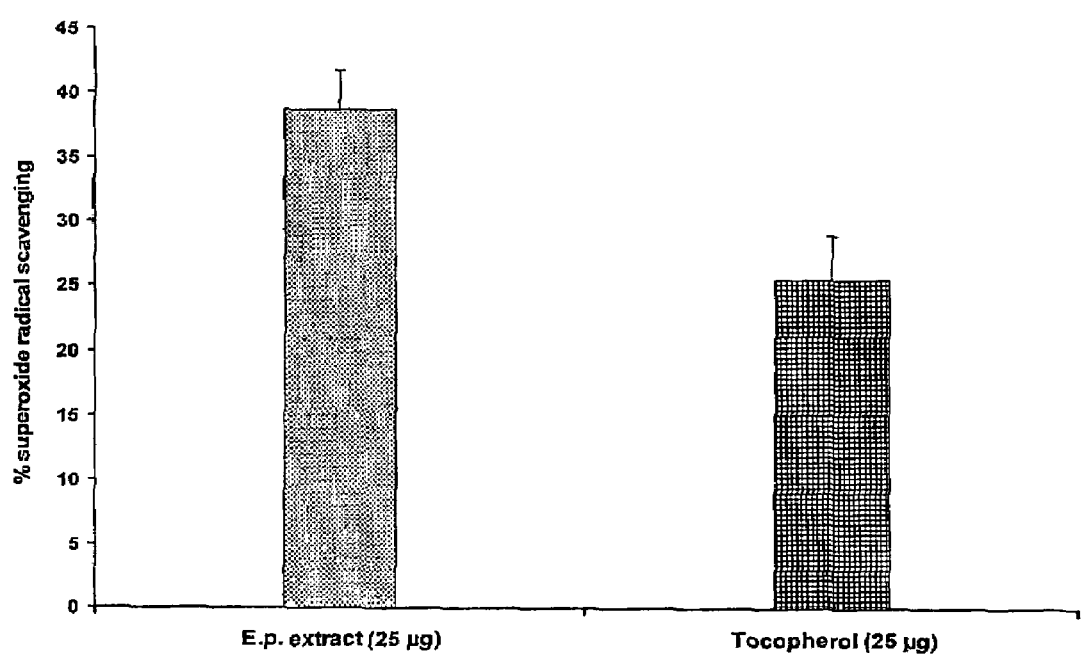

*Euphorbia prostrata* extract (25 µg) exhibited a superior superoxide radical scavenging activity of 38.70% in comparison to tocopherol (25 µg), which showed a similar activity of 25.54% (FIG. 9).

Wound Healing Activity

The wounds were developed by skin excision method in rats as described by Vishnu Rao et al., 1996. *Euphorbia prostrata* extract cream (1.75%) showed significant wound healing activity in comparison to placebo cream on Day 4, 8, and 12 in skin excision model in rats. The results are presented in table-2 & table-3.

TABLE 2

Gross examination of wounds in rats

| Observation time | Treatment | |
|---|---|---|
| | Control | *Euphorbia prostrata* extract cream |
| Day 4 | Bloody, raw, wet | Red, partially wet, partially healed (epithelium regeneration started) |
| Day 8 | Scar formation started, partially wet, red | Complete Scar formed, dry |
| Day 12 | Scar, not replaced with new skin | Scar, completely replaced with new skin, complete healing of the wound |
| | | Placebo cream |
| Day 4 | Bloody, raw, wet | Red, wet, partially healed |
| Day 8 | Scar formation started, partially wet, red | Scar formation started, partially wet |
| Day 12 | Scar, not replaced with new skin | Scar, replacement with new skin started |

TABLE 3

Percent decrease in wound area in rats

| | Treatment | | | |
|---|---|---|---|---|
| | Euphorbia prostrata extract Group | | Placebo Group | |
| Observation time | Control | Euphorbia prostrata extract cream | Control | Placebo cream |
| Day 4 | 46.61 ± 4.68 | 57.14 ± 2.24* | 34.95 ± 3.35 | 37.22 ± 9.79 |
| Day 8 | 74.60 ± 2.25 | 84.67 ± 1.88* | 74.66 ± 2.56 | 74.29 ± 6.02 |
| Day 12 | 88.04 ± 1.61 | 95.64 ± 0.52* | 91.43 ± 0.68 | 92.31 ± 1.62 |

*$p < 0.05$ as compared to control group

Mechanism of Anti-Hemorrhoidal Activity Of The Extract:

*Euphorbia prostrata* extract mainly comprises of flavonoids (apigenin-7-glucoside, luteolin-7-glucoside), ellagic acid, gallic acid, and tannins. Phenolic compounds are widespread in the plant kingdom. The major groups of phenolic compounds are flavonoids and phenolic acids. They are one of the main constituents of several medicinal plants that have been used as folk medicine throughout the world. Interest has recently been focused on flavonoids and flavanoids because of their broad pharmacological activities. These flavonoids are well reported for analgesic, anti-inflammatory, antioxidant, antiangiogenic, anti-allergic, antiviral and antimutagenic activity (Lin et al., 2001; Formica and Regelson, 1995; Fotsis et al., 1997; Wang et al., 1998; Block et al., 1998). It is reported that apigenin is a most potent inhibitor of transcriptional activation of both COX-2 and iNOS (inducible nitric oxide synthase) enzyme in lipopolysaccharide activated RAW 264.7 macrophages. It is further suggested that suppression of transcriptional activation of COX-2 and iNOS by apigenin might mainly be mediated through inhibition of κB. Such type of modulation of COX-2 and iNOS by apigenin may be important in the prevention of carcinogenesis and inflammation (Liang et al., 1999). Further, it is also suggested that antioxidant property of apigenin-7-glucoside contributes to its anti-inflammatory activity in various animal models (Fuchs and Milbradt, 1993). Della Loggia et al., 1986 also reported that apigenin-7-glucoside and luteolin-7-galactoside shows a dose dependent inhibition of the oedematous response to croton oil. In $CCl_4$ induced peroxidation, apigenin and luteolin had shown significant antiperoxidative activity in rat liver microsomes (Cholbi et al., 1991). Xagorari et al., 2001 reported that luteolin inhibits protein tyrosin phosphorylation, nuclear factor-κB mediated gene expression and pro-inflammatory cytokine production in murine macrophages. Ellagic acid is one of the major constituents of *Euphorbia prostrata* extract also reported to suppress histamine release mediated by histamine liberators (compound 48/80, dextran and polymyxin B sulfate) in vivo (Bhargava and Westfall, 1969). Moreover, the anti-inflammatory effects of flavonoids comprise inhibition of histamine release, modulation of the prostanoids metabolism and antioxidant properties. It is speculated that analgesic, anti-inflammatory and antioxidant activity of various flavonoid components of *Euphorbia prostrata* extract (apigenin-7-glucoside, luteolin-7 -glucoside) and ellagic acid and/or gallic acid may contribute in healing of inflammatory tissue damage in hemorrhoidal conditions.

Phenolic acids are reported to activate intrinsic blood coagulation by activation of Hageman factor and cause a state of hypercoagulability. Although the hypercoagulable state persists for as long as 4 hours after i.v. administration, no thrombotic phenomenon has been reported (Girolami and Cliffton, 1967).

Vegetable tannins are water-soluble phenolic compounds including both hydrolysable and condensed tannins that are present in every food plant. Hydrolysable tannins contain either gallotannins or ellagiotannins that yield gallic acid or ellagic acid respectively on hydrolysis. It is well reported that tannic acid has antimicrobial properties, which is associated with the ester linkage between gallic acid and other sugar or alcohol groups (Chung et al., 1993; 1995).

From the anti-hemorrhoidal studies conducted in animals, it is evident that the *Euphorbia prostrata* extract has better efficacy than the purified flavonoids or other constituents alone.

The various studies conducted on *kuphorbia prostrata* extract are listed below in FIGS. 1-9.

FIG. 1: Effect of *Euphorbia prostrata* extract (E.p. extract) against carrageenan-induced hemorrhoids in rats.

FIG. 2: Effect of individual component of *Euphorbia prostrata* extract (E.p. extract) against carrageenan-induced hemorrhoids in rats.

FIG. 3: Effect of *Euphorbia prostrata* extract (E.p. extract) against carrageenan-induced paw oedema (oral).

FIG. 4: Effect of *Euphorbia prostrata* extract (E.p. extract) against carrageenan-induced paw oedema (topical).

FIG. 5: Effect of *Euphorbia prostrata* extract (E.p. extract) against acetic acid-induced chemonociception in mice.

FIG. 6: Effect of principal components of *Euphorbia prostrata* extract (E.p. extract) against acetic acid-induced chemonociception in mice.

FIG. 7: Effect of *Euphorbia prostrata* extract (E.p. extract) against carageenan-induced hyperalgesia in rats.

FIG. 8: Effect of *Euphorbia prostrata* extract (E.p. extract) on bleeding time in liver incision model.

FIG. 9: In vitro superoxide radical scavenging activity of *Euphorbia prostrata* extract (E.p. extract).

Safety Studies

Effect on Central Nervous System

The effect of *Euphorbia prostrata* extract on the central nervous system were assessed from acute studies of effect on the appearance and gross behavior of rats and mice, the performance of mice on a rotating rod, open field behavior in rats, locomotor activity in mice using actophotometer, rectal temperature in rats, forced swimming despair behavior in mice, pentobarbitone-induced sleeping time in mice. Behaviorally, *Euphorbia prostrata* extract was well tolerated by both mice and rats (up to 2000 mg/kg, p.o.) following single oral administration and following multiple dose oral administration (up to 130 mg/kg in mice for 28 days and up to 90 mg/kg in rats for 28 days). In diazepam-controlled mouse studies, *Euphorbia prostrata* extract did not (a) alter gross behavior; (b) impair motor co-ordination (totarod test); (c) impair motor activity using actophotometer after oral administration at doses 100, 200 and 400 mg/kg. In chlorpromazine-controlled rat study, *Euphorbia prostrata* extract did not alter rectal temperature at doses 100, 200, and 400 mg/kg. In imipramine-controlled mouse study, *Euphorbia prostrata* extract at doses 100, 200, and 400 mg/kg did not alter forced swimming despair behavior after single oral administration. Furthermore, *Euphorbia prostrata* extract did not interact with pentobarbitone-induced sleeping time at doses 100, 200, and 400 mg/kg in mice. In diazepam-controlled rat study, *Euphorbia prostrata* extract did not impair open field behavior (ambulatory and rearing behavior) at doses 100, 200, and 400 mg/kg.

Effect on Cardiovascular System

*Euphorbia prostrata* extract did not cause any change in normal ECG, blood pressure, and heart rate in rats following single oral administration up to 400 mg/kg and following multiple dose oral administration (up to 90 mg/kg in rats for 28 days).

Effect on Respiratory System

Daily oral administration of *Euphorbia prostrata* extract at dose 400 mg/kg for 7 days did not alter basal insufflation pressure of trachea in guinea pig on day 7.

Effect on Gastrointestinal System

Single oral administration of *Euphorbia prostrata* extract upto 400 mg/kg did not alter basal acid secretion and gastrointestinal integrity upon single administration upto 400 mg/kg in rats. In mice, there was no alteration in gut motility up to 400 mg/kg, p.o. of *Euphorbia prostrata* extract after 1 h of single dose oral administration.

Toxicological Studies

Single Dose Toxicity:

*Euphorbia prostrata* extract did not show mortality when administered up to 2000 mg/kg, p.o. in rats and mice.

Repeat Dose Toxicity:

Mice: Repeated administration (32.50 mg/kg, 65.0 mg/kg and 130.0 mg/kg, p.o.) of *Euphorbia prostrata* extract for 28 days to mice did not exhibit mortality (NOEL 130 mg/kg, p.o.).

Rats: Repeated administration (22.50 mg/kg, 45.0 mg/kg and 90.0 mg/kg, p.o.) of *Euphorbia prostrata* extract for 28 days to rats did not exhibit mortality (NOEL 90 mg/kg, p.o.). In another study, repeated administration of *Euphorbia prostrata* extract 428 mg/kg, p.o., for 14 days did not produce significant alterations in body weight, organ weights, biochemical, and histopathological changes in comparison to control animals.

Guinea pig: Repeated administration of *Euphorbia prostrata* extract up to 300 mg/kg, p.o. to guinea pigs for 14 days did not produce significant alterations in body weight, organ weights, biochemical, and histopathological changes in comparison to control animals.

Examples are provided below to illustrate the various aspects of the present invention. However, they do not intend to limit the scope of the present invention.

EXAMPLES

General Process of Manufacture of the Extract:

Qualified professionals collected the plant *Euphorbia prostrata* from various parts of India. The plant was identified and characterized according to WHO guidelines (WHO/TRM/91.4, Programme Traditional Medicines World Health Organization Geneva, 1991) and was dried under controlled conditions of temperature and humidity. The whole plant was ground to coarse powder. The coarse powder was extracted using a polar solvent like an alkanol or acetone with or without water. The extract was concentrated and washed with a non-polar solvent like a hydrocarbon or chlorinated hydrocarbon. The washed extract was optionally further extracted into a medium polar solvent like ethyl acetate or ethyl methyl ketone. The final extract was optionally dehydrated with a suitable dehydrating agent and dried, either in a tray drier or in a spray drier, milled to a powder form, sifted to the desired particle size and packed in a suitable container to protect from moisture.

Example 1

The powdered drug (500 kg) was packed in a S.S. extractor. The extraction was affected by percolation with 3000 lt. of 80% aqueous methanol at about 60° C. The process was repeated 5 times till the drug was exhausted. The aqueous-methanolic extracts were combined and concentrated by distillation.

The concentrated extract was washed with 5-10 volumes of hexane to remove the wax and fatty material. The washed extract was dried completely for several hours at 60° C. under vacuum. The final extract was milled to a fine powder, sifted for uniform particle size and packed to protect from the moisture.

Example 2

The powdered drug (700 kg) was packed in a S.S. extractor. The extraction was affected by percolation with 4500 lt. of methanol at about 60° C. The process was repeated 5 times till the drug was exhausted. The methanolic extracts were combined and concentrated by distillation. The concentrated extract was washed with 5-10 volumes of dichloromethane to remove the wax and fatty material. The washed extract was dried completely for several hours at 60° C. under vacuum. The final extract was milled to a fine powder, sifted for uniform particle size and packed to protect from the moisture.

Example 3

The powdered drug (350 kg) was packed in a S.S. extractor. The extraction was affected by percolation with 3000 lt. of 80% aqueous acetone at about 50° C. The process was repeated S times till the drug was exhausted. The aqueous-acetone extracts were combined and concentrated by distillation. The concentrated extract was washed with 5-10 volumes of hexane to remove the wax and fatty material. The washed extract was dried completely for several hours at 60° C. under vacuum. The final extract was milled to a fine powder, sifted for uniform particle size and packed to protect from the moisture.

Example 4

The powdered drug (500 kg) was packed in a S.S. extractor. The extraction was affected by percolation with 3000 lt. of 80% aqueous ethanol at about 60° C. The process was repeated 5 times till the drug was exhausted. The aqueous-ethanolic extracts were combined and concentrated by distillation. The concentrated extract was washed with 5-10 volumes of hexane to remove the wax and fatty material. The washed extract was again extracted with ethyl acetate. The ethyl acetate extract was dehydrated with anhydrous sodium sulphate and concentrated by distillation. The concentrated extract was dried completely for several hours at 60° C. under vacuum. The final purified extract was milled to a fine powder, sifted for uniform particle size and packed to protect from the moisture.

Example 5

The powdered drug (500 kg) was boiled with 2500 lt. of DM water for 4 hours. The aqueous extract was filtered and residue was again boiled with 1500 lt. of DM water for 2 hours and filtered. The pooled filtered extracts were concentrated using a falling film evaporator and then further dried completely for several hours at 60° C. under vacuum. The final purified extract was milled to a fine powder, sifted for uniform particle size and packed to protect from the moisture.

Process of Evaluation of the Extract

The extract of *Euphorbia prostrata* of the above-mentioned examples was characterised by High Performance Liquid Chromatography (HPLC). The HPLC was performed under following conditions and using Waters system equipped with M510 pumps and data station with Millenium software.

Mobile phase: A linear gradient of Mobile Phase A (2% acetic acid in Water) and Mobile Phase B (2% acetic acid in Acetonitrile) according to the following table:

| Time (minutes) | Mobile Phase 'A' % | Mobile Phase 'B' % | Comments |
|---|---|---|---|
| 0 | 90 | 10 | Equilibration |
| 0-2 | 90 | 10 | Isocratic |
| 2-30 | 65 | 35 | Linear Gradient |
| 30-35 | 65 | 35 | Isocratic |
| 35-40 | 90 | 10 | Linear Gradient |
| 40-45 | 90 | 10 | Isocratic |

Column: $C_{18}$ (250×4.6 mm/5 µm)
Flow Rate: 1 ml/min
Detector: UV absorbance at 335 nm The HPLC chromatogram showed a number of peaks, the major ones corresponding to gallic acid, ellagic acid, luteolin glucoside and apigenin glucoside. The two peaks corresponding to the flavonoid components luteolin glucoside and apigenin glucoside were used as the chemical and pharmacological marker for quantitation of the product. A sum of the two peaks was calculated corresponding to standard apigenin glucoside and the measure was expressed as the Total Flavonoids.

Capsule Compositions

Example 6

| Ingredient | mg/capsule |
|---|---|
| *Euphorbia prostrata* extract | 100.0 |
| Microcrystalline cellulose | 200.8 |
| Mannitol | 72.0 |
| Talc | 3.2 |
| Sodium starch glycollate | 12.0 |
| Colloidal silicon dioxide | 12.0 |

Procedure:
1) *Euphorbia prostrata* extract, microcrystalline cellulose and mannitol are sifted and mixed together.
2) Talc, sodium starch glycollate and colloidal silicon dioxide are passed through fine sieves individually and then mixed together.
3) The materials of step 1 and 2 are mixed.
4) The material of step 3 is filled into empty hard gelatin capsules at an average fill weight of 400 mg±2%.
5) The filled capsules are packed in air-tight packages.

Example 7

| Ingredient | mg/capsule |
|---|---|
| *Euphorbia prostrata* extract | 100.0 |
| Microcrystalline cellulose | 150.0 |
| Mannitol | 65.0 |
| Lactose | 50.0 |
| Talc | 3.0 |
| Sodium starch glycollate | 17.0 |
| Colloidal silicon dioxide | 15.0 |

Procedure:
1) *Euphorbia prostrata* extract, microcrystalline cellulose, lactose and mannitol are sifted and mixed together.
2) Talc, sodium starch glycollate and colloidal silicon dioxide are passed through fine sieves individually and then mixed together.
3) The materials of step 1 and 2 are mixed.
4) The material of step 3 is filled into empty hard gelatin capsules at an average fill weight of 400 mg±2%.
5) The filled capsules are packed in air-tight packages.

Example 8

| Ingredient | mg/capsule |
|---|---|
| *Euphorbia prostrata* extract | 100.0 |
| Microcrystalline cellulose | 50.0 |
| Mannitol | 65.0 |
| Lactose | 150.0 |
| Talc | 3.0 |
| Sodium starch glycollate | 17.0 |
| Colloidal silicon dioxide | 15.0 |

Procedure:
1) *Euphorbia prostrata* extract, microcrystalline cellulose, lactose and mannitol are sifted and mixed together.
2) Talc, sodium starch glycollate and colloidal silicon dioxide are passed through fine sieves individually and then mixed together.
3) The materials of step 1 and 2 are mixed.
4) The material of step 3 is filled into empty hard gelatin capsules at an average fill weight of 400 mg±2%.
5) The filled capsules are packed in air-tight packages.

Example 9

| Ingredient | mg/capsule |
|---|---|
| *Euphorbia prostrata* extract | 100.0 |
| Microcrystalline cellulose | 175.0 |
| Mannitol | 80.0 |
| Talc | 5.0 |

-continued

| Ingredient | mg/capsule |
| --- | --- |
| Sodium starch glycollate | 15.0 |
| Colloidal silicon dioxide | 25.0 |

Procedure:
1) *Euphorbia prostrata* extract, microcrystalline cellulose and mannitol are sifted and mixed together.
2) Talc, sodium starch glycollate and colloidal silicon dioxide are passed through fine sieves individually and then mixed together.
3) The materials of step 1 and 2 are mixed.
4) The material of step 3 is filled into empty hard gelatin capsules at an average fill weight of 400 mg±2%.
5) The filled capsules are packed in air-tight packages.

Example 10

| Ingredient | mg/capsule |
| --- | --- |
| *Euphorbia prostrata* extract | 100.0 |
| Microcrystalline cellulose | 135.0 |
| Starch | 25.0 |
| Dibasic calcium phosphate | 110.0 |
| Talc | 2.0 |
| Magnesium stearate | 3.0 |
| Sodium starch glycollate | 10.0 |
| Colloidal silicon dioxide | 15.0 |

Procedure:
1) *Euphorbia prostrata* extract, microcrystalline cellulose, starch and dibasic calcium phosphate are sifted and mixed well.
2) Talc, magnesium stearate, sodium starch glycollate and colloidal silicon dioxide are passed through fine sieves individually and then mixed together.
3) The materials of step 1 and 2 are mixed.
4) The material of step 3 is filled into empty hard gelatin capsules at an average fill weight of 400 mg±2%.
5) The filled capsules are packed in air-tight packages.

Example 11

| Ingredient | mg/capsule |
| --- | --- |
| *Euphorbia prostrata* extract | 100.0 |
| Microcrystalline cellulose | 90.0 |
| Lactose | 50.0 |
| Starch | 122.0 |
| Talc | 3.0 |
| Magnesium stearate | 3.0 |
| Croscarmellose sodium | 12.0 |
| Colloidal silicon dioxide | 20.0 |

Procedure:
1) *Euphorbia prostrata* extract, microcrystalline cellulose, lactose & starch are sifted and mixed together.
2) Talc, magnesium stearate, croscarmellose sodium and colloidal silicon dioxide are passed through fine sieves individually and then mixed together.
3) The materials of step 1 and 2 are mixed.
4) The material of step 3 is filled into empty hard gelatin capsules at an average fill weight of 400 mg±2%.
5) The filled capsules are packed in airtight packages.

Example 12

| Ingredient | mg/capsule |
| --- | --- |
| *Euphorbia prostrata* extract | 100.0 |
| Mannitol | 176.0 |
| Starch | 100.0 |
| Talc | 2.0 |
| Croscarmellose sodium | 5.0 |
| Sodium starch glycollate | 12.0 |
| Sodium stearyl fumarate | 5.0 |

Procedure:
1) *Euphorbia prostrata* extract, mannitol and starch are sifted and mixed together.
2) Talc, croscarmellose sodium, sodium starch glycollate and sodium stearyl furmate are passed through fine sieves individually and then mixed together.
3) The materials of step 1 and 2 are mixed.
4) The material of step 3 is filled into empty hard gelatin capsules at an average fill weight of 400 mg±2%.
5) The filled capsules are packed in air-tight packages.

Tablet Compositions

Example 13 (Uncoated Tablet)

| Ingredient | mg/tablet |
| --- | --- |
| *Euphorbia prostrata* extract | 100.0 |
| Microcrystalline cellulose | 120.0 |
| Mannitol | 80.0 |
| Croscarmellose sodium | 10.0 |
| Lactose | 66.0 |
| Talc | 4.0 |
| Colloidal silicon dioxide | 10.0 |
| Croscarmellose sodium | 10.0 |

Procedure:
1) *Euphorbia prostrata* extract, microcrystalline cellulose, mannitol, croscarmellose sodium and lactose are sifted and mixed together.
2) The material of step 1 is compacted.
3) The compacts of step 2 are passed through sieve and mixed.
4) Talc, colloidal silicon dioxide and croscarmellose sodium are passed through fine sieve and mixed together.
5) The material of step 3 is mixed with material of step 4.
6) The material of step 5 is compressed into tablets at an average weight of 400 mg±2%.
7) The tablets are packed in air-tight packages.

Example 14 (Film-Coated Tablet)

| Ingredient | mg/tablet |
|---|---|
| Core tablet composition | |
| *Euphorbia prostrata* extract | 100.0 |
| Microcrystalline cellulose | 120.0 |
| Mannitol | 80.0 |
| Croscarmellose sodium | 10.0 |
| Lactose | 66.0 |
| Talc | 4.0 |
| Colloidal silicon dioxide | 10.0 |
| Croscarmellose sodium | 10.0 |
| Film coating composition | |
| Hydroxypropyl methylcellulose (E-15) | 12.0 |
| Polyethylene glycol 400 (PEG 400) | 2.4 |
| Iron oxide red | 0.75 |
| Iron oxide yellow | 0.50 |
| Titanium dioxide | 0.25 |
| Isopropyl alcohol | q.s. (lost in processing) |
| Dichloromethane | q.s. (lost in processing) |

Procedure:

1) *Euphorbia prostrata* extract, microcrystalline cellulose, mannitol, croscarmellose sodium and lactose are sifted and mixed together.
2) The material of step 1 is compacted.
3) The compacts of step 2 are passed through sieve and mixed.
4) Talc, colloidal silicon dioxide and croscarmellose sodium are passed through fine sieve and mixed together.
5) The material of step 3 is mixed with material of step 4.
6) The material of step 5 is compressed into tablets at an average weight of 400 mg±2%.
7) Hydroxypropyl methylcellulose is dispersed in a mixture of isopropyl alcohol and dichloromethane with continuous mixing in homogenizer.
8) PEG 400 is added to the above solution of step 7 and mixed.
9) Iron oxide red, iron oxide yellow and titanium dioxide are passed through fine sieve and mixed.
10) The material of step 9 is added to material of step 8 and mixed for 30 minutes.
11) The core tablets are charged into the coating pan and coated with the coating solution of step 10 till an average tablet weight gain of ~3% is achieved.
12) The tablets are dried and packed in air-tight packages.

Cream Compositions

Example 15

| Ingredient | mg/gm |
|---|---|
| *Euphorbia prostrata* extract | 10.0 |
| Propylene glycol | 50.0 |
| Titanium dioxide | 10.0 |
| Stearic acid | 130.0 |
| Cetyl alcohol | 10.0 |
| Isopropyl myristate | 60.0 |
| Sorbitan stearate | 20.0 |
| Methyl paraben | 1.5 |
| Propyl paraben | 0.3 |
| Corn oil | 50.0 |
| Glycerin | 50.0 |
| Sorbitol solution | 30.0 |
| Veegum HV | 10.0 |
| Sodium CMC | 3.0 |
| Tween 80 | 15.0 |
| Purified water | q.s. |

Procedure:

1) *Euphorbia prostrata* extract, methyl paraben and propyl paraben are dissolved in propylene glycol; the mixture heated to 55-60° C.; titanium dioxide is added to it and stirred well.
2) Stearic acid, cetyl alcohol, isopropyl myristate, sorbitan stearate, and corn oil are heated to 70°-75° C.
3) In another vessel, sorbitol solution and Tween 80 are taken.
4) Veegum HV is separately hydrated in the water.
5) Sodium carboxymethyl cellulose (sodium CMC) is separately hydrated in glycerin.
6) The material of step 4 and step 5 are added to the material of step 3 and heated to 70°-75° C.
7) The material of step 2 and step 6 are mixed and cooled.
8) When the material of step 7 attains a temperature of 50°-55° C., the material of step 1 is added to it.
9) The mixture is allowed to cool to room temperature to obtain the cream.

Example 16

| Ingredient | mg/gm |
|---|---|
| *Euphorbia prostrata* extract | 10.0 |
| Propylene glycol | 50.0 |
| Titanium dioxide | 10.0 |
| Hard paraffin | 60.0 |
| Liquid paraffin | 10.0 |
| Isopropyl myristate | 30.0 |
| Span 60 | 20.0 |
| Methyl paraben | 1.5 |
| Propyl paraben | 0.3 |
| Corn Oil | 20.0 |
| Glycerin | 80.0 |
| Sorbitol solution | 50.0 |
| Veegum HV | 20.0 |
| Tween 80 | 15.0 |
| Purified water | q.s. |

Procedure:

1. *Euphorbia prostrata* extract, methyl paraben and propyl paraben are dissolved in propylene glycol; the mixture heated to 55-60° C.; titanium dioxide is added to it and stirred well.
2. Hard paraffin, liquid paraffin, isopropyl myristate, Span 60, and Corn Oil are heated to 70-75° C.
3. Veegum HV is hydrated in purified water; glycerin, Tween 80, and sorbitol is added to it; and the mixture is heated to 70°-75° C.
4. The material of step 2 is added to the material of step 3 with stirring and the mixture is allowed to cool to 55°-60° C.

5. The material of step 1 is added to the material of step 4, stirred, and allowed to cool to room temperature to obtain the cream.

17

| Ingredient | mg/gm |
| --- | --- |
| *Euphorbia prostrata* extract | 10.0 |
| Propylene glycol | 50.0 |
| Titanium dioxide | 10.0 |
| Glyceryl monostearate | 90.0 |
| Hydrogenated lanolin | 30.0 |
| Corn oil | 40.0 |
| Simethicone | 1.5 |
| Span 60 | 20.0 |
| Hydroxyethyl cellulose | 20.0 |
| Glycerin | 50.0 |
| Sorbitol | 30.0 |
| Sodium CMC | 1.5 |
| Propyl paraben | 0.3 |
| Methyl paraben | 1.5 |
| Tween 80 | 15.0 |
| Purified water | q.s. |

Procedure:
1. *Euphorbia prostrata* extract, methyl paraben and propyl paraben are dissolved in propylene glycol; titanium dioxide is added to it and stirred well.
2. Glyceryl monostearate, hydrogenated lanolin, corn oil, simethicane, and Span 60 are taken.
3. In cool purified water, hydroxyethyl cellulose is dissolved; sorbitol and Tween 80 is added to it and the mixture is heated to 70-75° C.
4. Separately sodium carboxymethyl cellulose (sodium CMC) is dispersed in glycerin and added to the material of step 3.
5. The material of step 2 is added to the material of step 3 and allowed to cool with stirring.
6. When a temperature of 50-55° C. is attained, the material of step 1 is added, stirred, and allowed to cool to room temperature to obtain the cream.

18

| Ingredient | mg/gm |
| --- | --- |
| *Euphorbia prostrata* extract | 10.0 |
| Beeswax | 50.0 |
| Liquid paraffin | 60.0 |
| Corn oil | 25.0 |
| Stearic acid | 110.0 |
| Cetyl alcohol | 10.0 |
| Titanium dioxide | 10.0 |
| Propylene glycol | 50.0 |
| Methyl paraben | 1.5 |
| Propyl paraben | 0.3 |
| Glycerin | 50.0 |
| Sorbitol Solution | 30.0 |
| Tween 80 | 15.0 |
| Purified water | q.s. |

Procedure:
1. *Euphorbia prostrata* extract, methyl paraben and propyl paraben are dissolved in propylene glycol; titanium dioxide is added to it and stirred well.
2. Beeswax, liquid paraffin, corn oil, stearic acid and cetyl alcohol are heated to 70-75° C.
3. Glycerin, sorbitol and Tween 80 is added to purified water and heated to 70°-75° C.
4. The material of step 2 is added to the material of step 3 and stirred.
5. The material of step 1 is added to the material of step 4 and allowed to cool to room temperature to obtain the cream.

19

| Ingredient | mg/gm |
| --- | --- |
| *Euphorbia prostrata* extract | 10.0 |
| Propylene glycol | 50.0 |
| Titanium dioxide | 10.0 |
| Stearic acid | 70.0 |
| Simethicone | 1.0 |
| Glyceryl monostearate | 60.0 |
| Cetosteryl alcohol | 20.0 |
| Cetyl alcohol | 10.0 |
| Sorbitan stearate | 20.0 |
| Methyl paraben | 1.5 |
| Propyl paraben | 0.3 |
| Glycerin | 50.0 |
| Sorbitol | 30.0 |
| Tween 80 | 15.0 |
| Xanthan gum | 10.0 |
| Purified water | q.s. |

Procedure:
1. *Euphorbia prostrata* extract, methyl paraben and propyl paraben are dissolved in propylene glycol; titanium dioxide is added to it and stirred well.
2. Stearic acid, simethicone, glyceryl monostearate, cetosteryl alcohol, cetyl alcohol, and sorbitan stearate are heated to 70°-75° C.
3. Glycerin, sorbitol, Tween 80 and purified water are heated to 70°-75° C.
4. Xanthum gum is dispersed in glycerin and added to the material of step 3.
5. The material of step 2 is added to the material of step 4 and allowed to cool.
6. The material of step 1 is added to the material of step 5 and allowed to cool to room temperature to obtain the cream.

Suppository Compositions

20

| Ingredient | gm/10 units |
| --- | --- |
| *Euphorbia prostrata* extract | 0.50 |
| Polyethylene glycol 4000 (PEG 4000) | 3.56 |
| Polyethylene glycol 1000 (PEG 1000) | 12.46 |
| Polyethylene glycol 400 (PEG 400) | 1.78 |
| Propylene glycol | 1.50 |
| Glycerin | 0.20 |

Procedure:
1) PEG 4000, PEG 1000 and PEG 400 are melted together and mixed well.

2) *Euphorbia prostrata* extract is dissolved in propylene glycol at 40-45° C. with constant stirring.
3) The material of step 2 is added to the material of step 1 and mixed well.
4) The material of step 3 is poured into suppository moulds and cooled.
5) Suppositories thus formed are removed from moulds and packed suitably.

21

| Ingredient | gm/10 units |
|---|---|
| *Euphorbia prostrata* extract | 0.5 |
| Propylene glycol | 4.5 |
| Emulsifying wax | 9.0 |
| Beeswax | 4.0 |
| Span 80 | 2.0 |

Procedure:
1) Emulsifying wax and beeswax are melted together and mixed.
2) Span 80 is added to the material of step 1 and mixed.
3) *Euphorbia prostrata* extract is dissolved in propylene glycol at 40-45° C. with constant stirring.
4) The material of step 3 is added to the material of step 2 and mixed well.
5) The material of step 4 is poured into suppository moulds and cooled.
6) Suppositories thus formed are removed from moulds and packed suitably.

22

| Ingredient | gm/10 units |
|---|---|
| *Euphorbia prostrata* extract | 0.5 |
| Propylene glycol | 1.5 |
| Witepsol - 45 | 16.0 |
| Cetyl alcohol | 1.0 |
| Beeswax | 1.0 |

Procedure:
1) Cetyl alcohol, beeswax and Witepsol-45 are melted together.
2) *Euphorbia prostrata* extract is dissolved in propylene glycol at 40-45° C. with constant stirring.
3) The material of step 2 is added to the material of step 1 and mixed well.
4) The material of step 3 is poured into suppository moulds and cooled.
5) Suppositories thus formed are removed from moulds and packed suitably.

Evaluation of Clinical Efficacy of Capsules and Cream

The effective dose of extract of *Euphorbia prostrate* in nociceptive and inflammatory animal models varied from 5-20 mg/kg in mice and rats. Moreover, the maximum tolerable dose is more than 2000 mg/kg in mice and rats. Based on body surface area to body weight ratios, the expected dose of extract of *Euphorbia prostrata* for human studies could be in between 50-200 mg for 60 kg human being (Paget and Barnes, 1964; Freireich et al., 1966). It is observed that the maximum human therapeutic dose (200 mg for 60 kg human being) is approximately 57 and 112 times less than the maximum dose employed in the acute toxicity studies in mice and rats respectively calculated based on body surface area to body weight ratios.

Results of the Clinical Trials Conducted at Ram Manohar Lohia Hospital (RML Hospital) and Lok Nayak Jay Prakash-Narayan Hospital (LNJP Hospital), New Delhi (India)

The optimal dose, efficacy, safety and patient tolerability of 50 and 100 mg capsule formulations of extract of *Euphorbia prostrata* in hemorrhoidal attacks was evaluated in a double blind, placebo controlled, prospective, comparative and a randomized study conducted at RML and LNJP hospitals at New Delhi, India. The duration of study was 8 months and protocol therapy was for 10 days.

A total of 125 patients entered the study, out of which 72 patients suffered from degree I hemorrhoids and 53 patients suffered from degree 11 hemorrhoids. The patients in each category were randomized into 3 treatment groups i.e. TDA, TDB and TDC (i.e. 50 mg, 100 mg and placebo capsules). All patients were evaluated on day 5 and day 10 of starting therapy. A follow up of 3 months was done.

The clinical examination was carried out to score the signs and symptoms i.e. proctorrhagia, anal discomfort, pain, anal discharge and proctitis at Day 0, Day 5 and Day 10. The degree of improvement on individual clinical parameters was also assessed from day 0, Day 5 and Day 10. The number of episodes of bleeding with bowel action and utilization of analgesics and topical medication as rescue medication was also assessed at Day 0, Day 5, and Day 10.

For statistical description, all patients were included in "Intent to treat" analysis. Kruskal Wallis test and Wilcoxan signed rank test for qualitative variables and paired t-test and one-way ANOVA for quantitative analysis were applied.

The study demonstrated that 100 mg capsule of extract of *Euphorbia prostrata* (TDB) and 50 mg capsule of extract of *Euphorbia prostrata* (TDA) was generally more effective than placebo (TDC) group in all the efficacy parameters of hemorrhoids.

All the groups tolerated the drugs well and showed minimal side effects. All the laboratory parameters were normal at baseline as well as at the end of the therapy in all the 3 treatment groups.

Previous studies have demonstrated the efficacy and safety of extract of *Euphorbia prostrata* in the treatment of hemorrhoids in an uncontrolled fashion. In this study, extract of *Euphorbia prostrata* in two doses i.e. 50 and 100 mg showed good efficacy in treatment of hemorrhoids. However clinically, TDB group (100 mg capsule) showed better results in overall therapeutic evaluation.

In Degree I hemorrhoids, certain parameters in TDA group showed better results. From the analysis it was found that out of the three treatment groups, maximum number of patients in TDB group underwent 5-day therapy. The prolonged 10-day therapy in TDA group might attribute to the better response in some parameters. However, at day 5, in few evaluation parameters i.e., and discomfort and proctorrhagia, complete recovery was found in maximum number of patients in TDB group.

When the assessment on the degree of improvement in overall signs and symptoms of hemorrhoidal attacks was done, highest number of patients in TDB group showed substantial improvement at both assessment day i.e. Day 5 and Day 10. Clinically TDB group showed the better decrease in bleeding episodes at both Day 5 and Day 10. At 3 months follow up; both treatment groups i.e. TDA and TDB groups were found to be quite effective in terms of non-reoccurrence of bleeding.

It was found that although bleeding reoccurred in slightly more number of patients in TDB group, no treatment was needed in highest number of patients in TDB than TDA group. It may be inferred from this that the intensity of bleeding was not so severe to require any treatment interference.

In Degree II hemorrhoids, of all the treatment groups, TDB showed better results in anal discomfort and proctitis at Day 5. In other parameters i.e., proctorrhagia, anal discharge and pain at prolapse, both TDA and TDB were comparable but better than TDC clinically.

Also, at Day 5, TDB proved to be a better drug in bringing about complete disappearance of signs and symptoms of hemorrhoidal attacks. The better results shown by TDB group at Day 5 than at day 10 may be attributed to the fact that of all the treatment groups, highest number of patients in TDB groups underwent 5-day therapy and did not require prolonged therapy of 10 days. At 3 months follow up analysis; TDB was found to be better in all the aspects.

The use of rescue medication in Degree I and Degree II hemorrhoids was seen in lesser number of patients in TDB group at the end of therapy i.e. Day 10. The impact of rescue medication might also explain some better results seen with lesser dose of 50 mg (TDA) as compared to high dose 100 mg (TDB) in few parameters.

The invention claimed is:

1. A pharmaceutical composition for the treatment of an anorectal or colonic disease or condition which is a hemorrhoid, fissure, crack, fistula, abscess or inflammatory bowel disease comprising from 0.1% to 99% by weight of an extract of the plant *Euphorbia prostrata* said extract containing flavonoids and phenolic compounds, wherein the flavonoids are apigenin-7-glycoside; luteolin-7-glycoside; apigenin; luteolin; and quercetin; wherein apigenin-7-glycoside is about 1-4% by weight of the extract; luteolin-7-glycoside is about 0.3-2% by weight of the extract; apigenin is about 0.001-0.3% by weight of the extract; luteolin is about 0.001-0.3% by weight of the extract; and quercetin is about 0.001-0.3% by weight of the extract; and wherein the phenolic compounds are ellagic acid, gallic acid, and tannins; wherein the ellagic acid is about 1-15% by weight of the extract; gallic acid is about 1-12% by weight of the extract and tannins are about 1-10% by weight of the extract; said composition optionally comprising one or more additional therapeutic agents.

2. The pharmaceutical composition as claimed in claim 1, wherein the extract comprises about 2.5-3.5% by weight of apigenin-7-glycoside; 0.5 -1.5% by weight of luteolin-7-glycoside; 0.05-0.2% by weight of apigenin; 0.05-0.2% by weight of luteolin,; 0.05-0.2% by weight of quercetin; 4-15% by weight of ellagic acid,; 4-12% by weight of gallic acid; and about 3-8% by weight of tannins.

3. The pharmaceutical composition as claimed in claim 1, wherein the composition further comprises one or more pharmaceutically acceptable carriers, pharmaceutically acceptable bases or combinations thereof.

4. The pharmaceutical composition as claimed in claim 1 further comprising one or more therapeutic agents selected from astringents, anesthetics, vasoconstrictors, protectants, counterirritants, keratolytics, anti-cholinergics, wound healing agents and anti-microbial agents.

5. The pharmaceutical composition as claimed in claim 4, wherein the astringents are selected from the group consisting of calamine, zinc oxide, *hamamelis* water, bismuthresorcinol compound, bismuth subgallate, Peruvian balsam, aluminium chlorohydroxy allantoinate, and tannic acid or in a combination thereof.

6. The pharmaceutical composition as claimed in claim 4, wherein the anesthetics are selected from the group consisting of benzocaine, diperodon, pramoxine, camphor, dibucaine, phenol, tetracaine, and phenacaine or a combination thereof.

7. The pharmaceutical composition as claimed in claim 4, wherein the protectants are selected from the group consisting of aluminium hydroxide gel, calamine, cocoa butter, cod or shark liver oil, starch, white petroleum, wool alcohol, zinc oxide, vegetable or castor oil, polyethylene glycol, and propylene glycol or a combination thereof.

8. The pharmaceutical composition as claimed in claim 4, wherein the wound healing agents are selected from the group consisting of vitamin A, vitamin D, Peruvian balsam, and cod liver oil or a combination thereof.

9. The pharmaceutical composition as claimed in claim 4, wherein the keratolytics are selected from the group consisting of aluminium chiorohydroxy allantoinate and resorcinol, or a combination thereof.

10. The pharmaceutical composition as claimed in claim 1, wherein the composition is in the form of a cream, ointment, solution, spray, foam, suppository, medicated pad, bandage, powder, suspension, film, flake, oral hard gelatin capsule, soft gelatin capsule, coated tablet, uncoated tablet, modified release dosage form, liquid, lozenge, buccal or sublingual dosage form, wafer, caplet, or parenteral dosage form to be infiltered at the site of the injection.

11. A process for preparing a pharmaceutical composition for the treatment of anorectal or colonic disease comprising of an extract of the plant *Euphorbia prostrata* containing flavonoids and phenolic compounds, wherein the flavonoids are apigenin-7-glycoside; luteolin-7-glycoside; apigenin; luteolin; and quercetin; wherein apigenin-7-glycoside is about 1-4% by weight of the extract; luteolin-7-glycoside is about 0.3-2% by weight of the extract; apigenin is about 0.001-0.3% by weight of the extract; luteolin is about 0.001-0.3% by weight of the extract; and quercetin is about 0.001-0.3% by weight of the extract; and wherein the phenolic compounds are ellagic acid, gallic acid, and tannins; wherein the ellagic acid is about 1-15% by weight of the extract; gallic acid is about 1-12% by weight of the extract and tannins are about 1-10% by weight of the extract by weight, with one or more pharmaceutically acceptable carriers and bases and, optionally with one or more additional therapeutic agents, comprising the steps of:
   a) drying the plant *Euphorbia prostrata,*
   b) making a powder from the dried plant,
   c) extracting the powder with a polar solvent repetitively to obtain an extract,
   d) distilling the extract to obtain a concentrated extract,
   e) washing the concentrated extract with a non-polar organic solvent,
   f) optionally re-extracting the washed polar extract in a medium polarity organic solvent selected from the group consisting of ethyl acetate, ethyl methyl ketone, butanol or mixture thereof and, distilling the extract followed by dehydrating the extract, and
   g) drying the extract and optionally adding one or more pharmaceutically acceptable carriers, bases or a combination thereof.

12. A method of treatment of an anorectal or colonic disease or condition which is a hemorrhoid, fissure, crack, fistula. abscess or inflammatory bowel disease comprising administering a pharmaceutical composition according to claim 1 to a patient in need thereof.

* * * * *